US006638044B2

United States Patent
Rodriguez

(10) Patent No.: US 6,638,044 B2
(45) Date of Patent: Oct. 28, 2003

(54) APPARATUS FOR FORMING COMPOSITE PELLETS FOR THE CONTROLLED RELEASE OF THE ACTIVE INGREDIENT IN THE TREATMENT OF HUMANS OR ANIMALS

(75) Inventor: Lorenzo Rodriguez, Bologna (IT)

(73) Assignee: Ascor Chimici S.r.l., Bertinoro (Forli) (IT)

(*) Notice: Subject to any disclaimer, the term of this patent is extended or adjusted under 35 U.S.C. 154(b) by 0 days.

(21) Appl. No.: 10/023,764

(22) Filed: Dec. 21, 2001

(65) Prior Publication Data

US 2002/0081335 A1 Jun. 27, 2002

(30) Foreign Application Priority Data

Dec. 22, 2000 (IT) .................................... RN2000A0051

(51) Int. Cl.[7] .................................................. B29B 9/00
(52) U.S. Cl. .............................. 425/5; 425/7; 425/72.1; 264/4.3
(58) Field of Search .......................... 425/5, 6, 7, 130, 425/131.1, 72.1; 264/4.3, 4.4, 15, 4.6

(56) References Cited

U.S. PATENT DOCUMENTS

| | | | |
|---|---|---|---|
| 2,929,106 A | | 3/1960 | Snow et al. |
| 3,015,128 A | * | 1/1962 | Somerville, Jr. ............... 425/5 |
| 3,607,993 A | * | 9/1971 | Tuttle ............................. 264/8 |
| 3,632,257 A | * | 1/1972 | Ashizawa .................... 425/222 |
| 4,212,837 A | | 7/1980 | Oguchi et al. |
| 4,736,527 A | * | 4/1988 | Iwamoto et al. ............... 34/594 |
| 5,269,980 A | * | 12/1993 | Levendis et al. ............... 264/9 |
| 5,487,916 A | | 1/1996 | Christensen |
| 5,718,764 A | | 2/1998 | Walter |
| 6,063,313 A | | 5/2000 | Briskin et al. |

FOREIGN PATENT DOCUMENTS

| | | |
|---|---|---|
| GB | 415456 | 8/1934 |
| GB | 2 155 360 | 9/1985 |
| GB | 2 192 128 | 1/1988 |
| JP | 52 058755 | 5/1977 |
| JP | 54041961 | 4/1979 |
| WO | WO 97/18839 A1 | 5/1997 |
| WO | WO 99/39692 A2 | 8/1999 |

OTHER PUBLICATIONS

Abstract of Publication No. 59059410, Published Apr. 5, 1984.

* cited by examiner

Primary Examiner—Robert Davis
Assistant Examiner—Joseph S Del Sole
(74) Attorney, Agent, or Firm—Browdy and Neimark, P.L.L.C.

(57) ABSTRACT

An apparatus for forming composite pellets containing active ingredients encapsulated in encapsulating material for the controlled release of the active ingredient in the treatment of humans, animals or plants that is capable of the following steps: producing solid granules containing encapsulating material and active ingredient; generating a flow of granules; heating the granules in flight so as to melt a portion of encapsulating material located at the surface of each granule, of melted encapsulating material spreading on the surface of each granule to form a substantially uniform surface layer so as to confer on the granules the form of pellets; cooling the pellets in flight so as to solidify at least the surface layer; collecting the pellets.

72 Claims, 4 Drawing Sheets

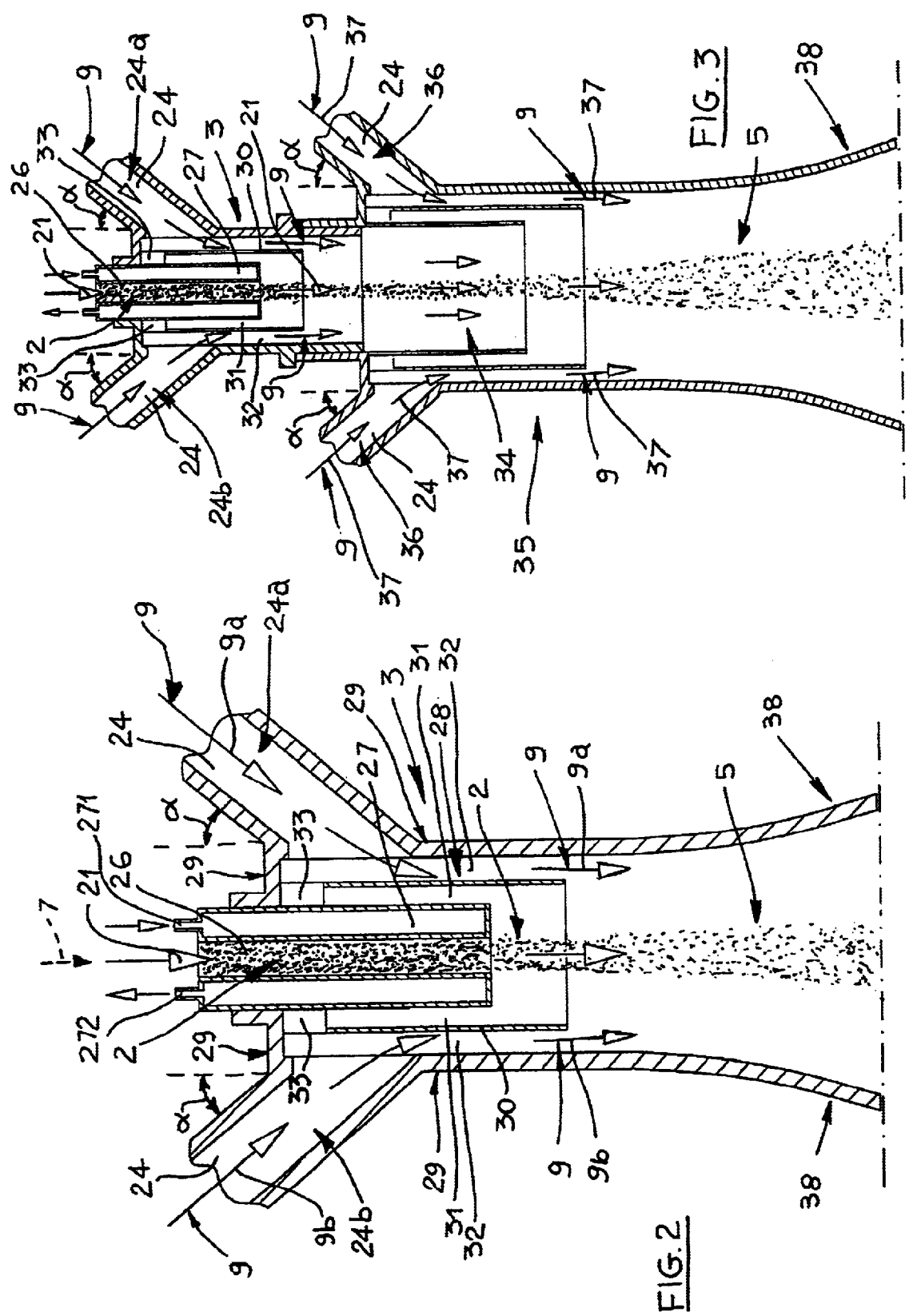

APPARATUS FOR FORMING COMPOSITE PELLETS FOR THE CONTROLLED RELEASE OF THE ACTIVE INGREDIENT IN THE TREATMENT OF HUMANS OR ANIMALS

BACKGROUND OF THE INVENTION

The present invention relates to a method and an apparatus for forming composite pellets containing active ingredients of the pharmaceutical type and/or nutritional complements or cosmetics, encapsulated in encapsulating material so as to control the release of the active ingredient in the treatment of humans or animals. The invention also relates to the composite pellets containing said active ingredients.

The practice of encapsulating pharmaceutical and/or nutritional complements in encapsulating materials (generally, but not exclusively, with low melting point), to make composite pellets to be administered, generally orally but also by other means, in therapeutic treatments or to supplement the diet of animals or humans is a well known practice. The encapsulating materials are substantially designed to control the release of the active ingredient (i.e. slowing or accelerating the release of the active ingredient in the best way and where it is truly useful), as well as to reduce the risk, whilst handling, transporting and administering the composite pellets, of polluting the environment with the active ingredient, which is released in the form of a powder and which may mix with other substances. In addition, an encapsulating material may also modify the taste of an active ingredient, to make it more acceptable when taken orally.

Normally, to slow down the releasing action, the encapsulating materials usually used are lipophilic materials which are solid at ambient temperature and have a low melting point. They include beeswax, carnauba wax or other types of wax, stearic acid, monoglycerides, diglycerides, triglycerides or other substances which are not digestible in the stomach but can be chemically attacked only by biliary and pancreatic fluids in the intestine.

Thanks to this property, the pellets containing a pharmacological and/or nutritionally complementing active ingredient are gastro-resistant and the release of the active ingredient may be delayed (an interval as long as two hours may elapse from the time of ingestion to the time the pellets reach the intestine) and/or prolonged (the intestinal fluid requires a certain amount of time in order to chemically attack and disintegrate the encapsulating material, and to reach all of the active ingredient content).

Many situations are known in which the release of the active ingredient must be delayed and prolonged in order to treat diseases in humans or to provide an effective complement to human nutrition.

In the field of animal treatment, the slowed release of the active ingredient may be used to complement with vitamins the nutrition of ruminants such as cattle. In this case, the vitamins must not be made available during the first digestive cycle, when they would be absorbed only by the bacterial flora needed by the animal to digest grass and would not be of any use to the animal itself.

To achieve less pronounced slow-downs, digestible non gastro-resistant materials may be used.

Conversely, to accelerate the release of active ingredients, the encapsulating materials used are usually water-soluble substances such as polymers which may also have low melting points (for example, polyethylene glycols or polyvinylpyrrolidone), and sugars, preferably also with a low melting point (for example, xylitol).

In the context of the present invention, the active ingredient may not only be a pharmaceutical and/or a nutritional complement, but also a cosmetic.

Within the specific field of current pharmaceutical technology, a method known as "spray-congealing method" is used to make composite pellets to be taken orally by humans or animals and consisting of pharmaceuticals and/or nutritional complements as active ingredients encapsulated in a low-melting material which controls the release of the active ingredient. In this method, the low melting temperature material is melted in a tank and maintained in the liquid state while it is uniformly mixed with one or more active ingredients (by means of a stirrer). If the active ingredient is soluble in the low melting temperature material, a solution is obtained, otherwise a suspension is obtained. The liquid mixture thereby obtained is sent to an atomizer or nebulizer and is then sprayed into a chamber that is maintained at ambient temperature or cooled. As they fall inside the cooled chamber, the droplets of melted mixture solidify and collect on the bottom of the chamber in the form of composite pellets.

The liquid atomizers or nebulizers may be of many different types, operating by centrifugal force (i.e. with rotating disks on which the melted mixture is made to fall), by compressed air, by high injection pressure of the melted mixture without using air, or by nebulizing fluid (air, inert gas or liquid).

The droplets of liquid mixture in the chamber may be cooled by maintaining the chamber at least at ambient temperature through cooling coils or by contacting the droplets with jets of cold inert gas (for example, a liquid nitrogen spray).

The method described above has several drawbacks.

In particular, the production of a large batch of pellets requires melting a large quantity of low melting point material and to do so requires a system of considerable size and a long time. Moreover, once the material is melted, the active ingredient must be mixed with it uniformly and in the proper proportions. To avoid variations in the concentration of the active ingredient in the pellets in the same batch, due to inconsistent distribution of the active ingredient (because of poor mixing or the re-depositing of the suspended particles of a non soluble active ingredient), this operation also takes a very long time and requires complex stirring mechanisms.

The mixture must be maintained in the melted state and under conditions of maximum homogeneity until the end of the step of spraying it into the cold chamber. This, too, requires a certain amount of time.

Thus, the mixed active ingredients remain in conditions of relatively high temperature (corresponding to the melting point of the encapsulating material) for a considerable length of time. Considering that low melting point materials generally melt at temperatures over 50° C. and that many of them do not melt at temperatures below 80° C., the active ingredients may degrade over time, leading to unacceptable variations in the quality of the pellets in a same batch. Many active ingredients are heat sensitive and, if heated for many hours, react and degrade at a rate that increases with increasing temperature (reaction speed approximately doubles for every 10° C. of temperature increase).

Therefore, it is virtually impossible to use bioactive ingredients such as yeasts, cells, enzymes, proteins, which are becoming increasingly common both in pharmaceuticals and in nutritional complements for humans as well as animals.

Further, the spray-congealing method also makes it impossible to use encapsulating materials whose melting points are not low, as these require even higher temperatures and, potentially, even longer processing times before they are sprayed than materials with low melting points.

The percentage weight of active ingredient that can be encapsulated in the pellets is generally very low (usually around 30%). Higher percentages of active ingredient (even if mixed in a material with low melting point in the liquid state) would give rise to a material in paste or "sludge" form. Even in the best of cases, this material could not be suitably atomized and the result would be poor quality pellets with irregular shape and size and with non-uniform composition and with certain amounts of active ingredient being deposited and consequently lost. In the worst of cases, the liquid atomizer or nebulizer would also be obstructed or clogged up.

The jet of droplets of melted material obtained by the atomizers and nebulizers is substantially proportional in length to its flow rate. Given the high speed at which the liquids are emitted by a nebulizer, to obtain high pellet production rates (in the order of a few kilograms per minute) without running the risk that the pellets reach the collection point still in the melted or semi-liquid state, adhering to the sides of the chamber, the chamber must be of considerable size, often with a large, tower-like structure.

High productivity installations, therefore, are bulky and hence can also be extremely costly, if constructed to meet the requirements necessary to comply with the quality standards for the production of drugs or diet supplements for human consumption (for instance, the use of controlled or inert atmospheres, tightness against external pollutants, protection of the environment from toxic spills, the use of stainless or special steel structures, etc.).

For this reason, the spray-congealing method is generally limited to products for animal use (in which the required quality standards described above are less strict), to research laboratories and to small-scale production of drugs and/or nutritional complements also for human consumption where the selling price of the product is so high as to make the use of very expensive equipment economically feasible.

Document U.S. Pat. No. 4,212,837 discloses a method for forming spherical particles of thermoplastic materials where a stream of gas with particles of thermoplastic material dispersed therein is blown from a peripheral region into a jet of hot pressurized gas to form the thermoplastic spherical particles. The document also describes an apparatus which implements the method. The apparatus includes means for discharging a jet of pressurized hot gas from an outlet port and means for ejecting a stream of gas having thermoplastic particles dispersed in it from at least one opening towards the jet of pressurized hot gas. This method is used to make non-composite spherical particles or pellets made from a single thermoplastic material. If applied to the field of the present invention, it presents several drawbacks, as found by the applicant in a number of experiments it has conducted. In particular, the particles ejected against the jet of hot gas tend to be dispersed in all directions by the jet of hot gas, with the consequent risk of prolonged contact of the particles with the heated surfaces of the apparatus. This means that oversize apparatus is required to avoid this problem. Moreover, since heat transfer efficiency is low, the heating time and/or the temperature of the hot gas must be increased. Doing this, however, creates the problem of degrading the active principle.

SUMMARY OF THE INVENTION

The aim of the present invention is to overcome the aforesaid drawbacks by providing a highly efficient method for forming composite pellets containing active ingredients encapsulated in encapsulating material so as to control the release of the active ingredients, the method reducing to a minimum the exposure of the active ingredients to high temperature and permitting the use of encapsulating materials whose melting points are not low of active ingredients that are heat sensitive.

Another aim of the present invention is to provide a method for forming composite pellets containing active ingredients encapsulated in encapsulating material so as to control the release of the active ingredient, the method allowing the production of pellets where the percentage weight of the active ingredient is preponderant.

Another aim of the present invention is to provide a method for forming composite pellets containing active ingredients encapsulated in encapsulating material so as to control the release of the active ingredient, the method allowing high productivity and uniformity within the batches of pellets made.

A further aim of the present invention is to provide a method for forming composite pellets containing active ingredients encapsulated in encapsulating material so as to control the release of the active ingredient, the method being suitable for implementation using apparatus of small size and low cost, thereby limiting the cost of the final product.

Yet another aim of the present invention is to provide an apparatus for forming composite pellets containing active ingredients encapsulated in encapsulating material so as to control the release of the active ingredient, the apparatus being suitable for implementing the method according to the invention.

Yet another aim of the present invention is to provide composite pellets containing active ingredients encapsulated in encapsulating material so as to control the release of the active ingredient, each pellet comprising a substantially uniform surface layer, composed mainly of material with a low melting point, and the active ingredient being concentrated mainly in the core of the pellet.

A further aim of the present invention is to provide composite pellets containing active ingredients encapsulated in encapsulating material so as to control the release of the active ingredient, and where the percentage weight of the active ingredient is preponderant.

These aims and others, which shall become more readily apparent in the course of the description that follows, are achieved, in accordance with the present invention, by a method and an apparatus as described in the accompanying claims for forming composite pellets containing active ingredients of the pharmaceutical type and/or nutritional complements or cosmetics, encapsulated in encapsulating material so as to control the release of the active ingredient in the treatment of humans or animals and by the composite pellets made using said method and apparatus.

BRIEF DESCRIPTION OF THE DRAWINGS

The invention will now be described in more detail with reference to the accompanying drawings, which illustrate a non-limiting preferred embodiment of it.

FIG. 2 schematically illustrates a detail showing an embodiment of the emission area.

FIG. 3 shows a variant of the embodiment of FIG. 2, in which the composite granules are heated in two stages.

DESCRIPTION OF THE PREFERRED EMBODIMENTS

Figure 1:
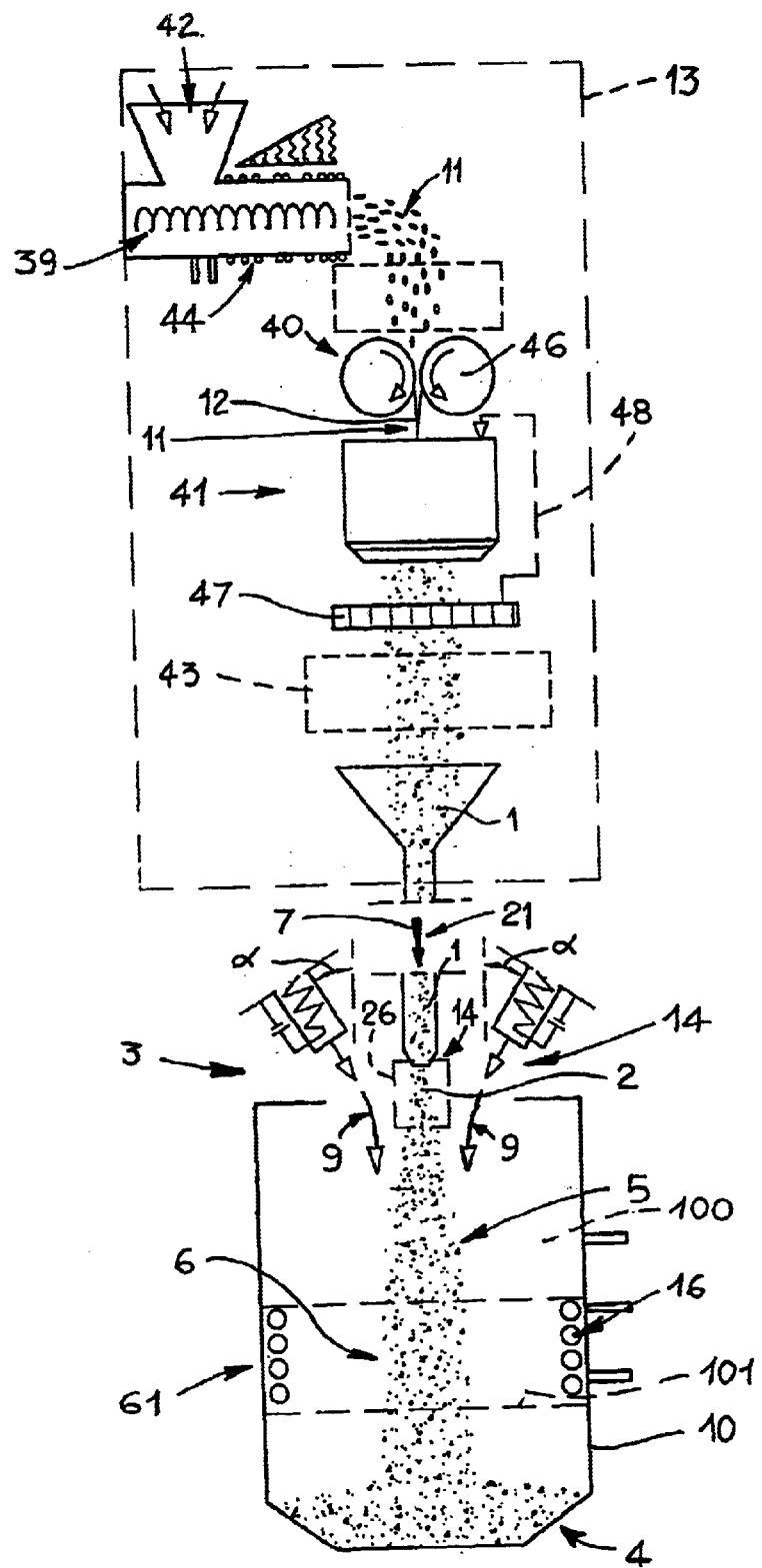
FIG. 1 schematically represents an apparatus according to the present invention, implementing the method of the present invention.

With reference to the drawings, a method for forming composite pellets containing active ingredients of the pharmaceutical type and/or nutritional complements or cosmetics, encapsulated in encapsulating material so as to control the release of the active ingredient in the treatment of humans or animals comprises a step of producing substantially solid composite granules 1, containing predetermined percentage weights of at least one encapsulating material and at least one active ingredient, mixed together in substantially homogeneous fashion. In general, there may be a mixture of different encapsulating materials and/or a mixture of two or more active ingredients, depending on requirements.

In a subsequent step, at least one flow 2 of the granules 1 is generated along a route from an emission area 3 to a collection area 4. In a further step, the flow 2 of the granules 1 is conveyed into at least one jet 9 of a first heated gaseous fluid which heats the granules 1 in flight for at least a first segment 5 of the route and to at least a first temperature. The jet 9 of the first heated gaseous fluid, starting from the emission area 3, encloses the flow 2 of the granules 1 on at least two opposite sides and in a substantially laminar fashion for at least one first fraction of the first segment 5 of the route in substantially the same direction of motion as the jet 9 and the flow 2, tending to trap within it the flow 2 of the granules 1, so as to minimize the risk of prolonged contact of the granules 1 with heated surfaces and to improve the efficiency of heat transfer, the first temperature being high enough to melt at least a portion of encapsulating material located at the surface of each granule 1. The portion of encapsulating material that is melted spreads on the surface of each granule 1 and thus forms a substantially uniform surface layer conferring on the granules 1 the form of pellets. Once this transformation has taken place, the granules 1 can be referred to either as "pellets" or as "granules". In particular, the term "pellets" is used to denote the granules 1 that have already undergone the transformation.

In a subsequent step, the previously obtained pellets are cooled in flight for at least a second segment 6 of the route, to at least a second temperature, low enough to cause at least the surface layer to solidify.

Lastly, the pellets are collected at the collection area 4.

The novel aspect of the method lies precisely in the fact that, as they flow, the solid granules 1 (which comprise encapsulating material and active ingredient mixed in the desired proportions in substantially homogeneous fashion) are heated individually and with high efficiency, mainly at their surfaces, by keeping them trapped as much as possible within the substantially laminar flow generated by the jet 9, thus making the heating process extremely rapid and efficient. The pellets formed in this way exhibit a substantially uniform surface layer substantially composed of encapsulating material and in which the concentration of active ingredient is less than in the core.

As stated, the typical behavior of the first heated gaseous fluid within the jet 9 renders in-flight heating very efficient.

The gaseous fluid may be chemically inert with respect to the active ingredient and/or the encapsulating material. Examples of the gaseous fluid that can be used are, again by way of non exhaustive example, nitrogen, argon, air. The gaseous fluid used can be filtered, purified or sterile.

For the in-flight heating with gaseous fluid, steam can also be used. This increases efficiency thanks to its high heat capacity. Under equal conditions of flow, steam is able to transmit a greater quantity of heat to the granules 1, allowing process times to be further reduced. However, it also has the defect of moistening the finished product and causing condensation in the apparatuses used. The use of steam, thus, requires suitable corrective measures.

The process time in this case depends not only on the size of the granules 1, but also on the type of the second gaseous fluid and on its temperature. In general, the first gaseous fluid might be produced even at high temperatures (for instance even around 300° C., as in a normal hairdryer, obviously appropriately dimensioned). It is important that the granules 1 come into contact with the gaseous fluid when they cannot be damaged by it (for instance when the fluid has already partially cooled and the temperature has dropped, or when the gaseous fluid used for heating rapidly loses heat in the flow 2 of granules 1, so that the granules 1 are at tolerable temperatures for most of the route they follow).

Advantageously, the present invention makes it possible to heat the first gaseous fluid to a temperature that is higher than the melting temperature of the encapsulating material, but in such a way that the difference between the two temperatures can be between 20° C. and 40° C., without adversely affecting the efficiency of the process.

The temperature of the gaseous fluid used for heating the granules 1 in flight must generally be optimized according to an optimal relation between the following parameters: nature of the encapsulating material, size of the granules 1, properties of the active ingredient, velocity of the fluid, time of flight or desired duration/length of the route. By appropriately optimizing these parameters, and given the small quantity of material to be heated on each granule 1 to obtain the result and the large surface area per unit of mass available for the heat exchange, the length of time in which the active ingredient is exposed to a high temperature is considerably reduced (a negligible fraction of the corresponding time required in the spray-congealing method described above), thus allowing heat-sensitive active ingredients to be safely treated. The required exposure times can be reduced to around 0.5 seconds or even less. It is also possible to reduce the first segment of the route even to lengths of around 30 cm. The times needed to cover such distances can be extremely short, minimizing the probability of degradation of the active ingredient.

Use of the jet 9 of the first heated gaseous fluid for heating the granules 1 in flight also produces a drying/dehumidifying effect on the granules 1 themselves, if the fluid in use is not steam, but a dry gas.

In the transitory phase between the moment the melted encapsulating material spreads near the surface to the moment it is cooled, the surface heating may cause the active ingredient to degrade, but this degradation can be minimized and made to affect only a small part of the active ingredient located at the surface of the granule 1 by suitably calibrating the dimensions of the starting granules 1 and the heating temperature. Most of the active ingredient contained in the core is not degraded. Moreover, the fact that prolonged contact between the granules 1 and the heated surfaces can be avoided thanks to the substantially laminar flow of the jet 9, which encloses within it the flow 2 of the granules 1, is important because prolonged contact with the heated surfaces can lead to the damaging or charring of the granules 1 or of the pellets into which they have been transformed, as well as to risks of fire or precipitation of the active ingredient in the case of biphasic systems. Biphasic systems, such as those originated from insoluble active ingredients, pose a problem because they might tend to separate. However, this problem is minimal, depending both on the type of encapsulating material used and on the depth to which the encapsulating material tends to melt in the granule 1, since the time interval between heating in flight (and, hence, the corresponding melting) and cooling in flight is extremely short.

Moreover, given the reduced exposure times, it is possible to use not only encapsulating materials with low melting points, but also other materials with higher melting points. The encapsulating materials can be any of the following, listed purely as non-limiting examples: low melting point, lipophilic materials that are solid at ambient temperature, such as beeswax, carnauba wax, other types of wax, stearic acid, monoglycerides, diglycerides, triglycerides and other substances which are not digestible in the stomach, but can be chemically attacked only by biliary and pancreatic fluids in the intestine; digestible, non gastro-resistant substances; water-soluble substances such as polymers (for example, polyethylene glycols and polyvinylpyrrolidone) which may also have low melting points, and sugars, preferably also with low melting point (for example, xylitol). In cosmetic treatments, any polymers can be used provided they are hypoallergenic and not harmful to health.

The softening of the encapsulating material may occur at a low temperature (for example, about 37° C. in the case of cocoa butter) or at a higher temperature (>80° C. in the case of carnauba wax). Normally, it occurs at temperatures between 65° C. and 90° C., as is the case for the overwhelming majority of waxes, but, depending on the material, it may occur at even higher temperatures.

Since the hot material to be cooled is finely dispersed, located primarily on the surface of pellets to be cooled in flight (with the result that there is only a small quantity of material to be cooled on each pellet), the in-flight cooling step may also be short, which in turn means that the size of the apparatus required to contain the route of the flow 2 can be greatly reduced.

This, combined with suitable means (described in more detail below) for increasing the heating efficiency of the granules 1 in flight allows the route of the flow 2 of granules 1 which are transformed into pellets to be reduced in length to around one meter or less. Thus, the method of the present invention can be implemented by apparatus of very small size, which minimizes costs and not only allows the route of the flow 2 of granules 1 to be easily contained in a controlled atmosphere, but also allows sealed structures to be made so as to prevent contamination of the outside environment.

The cooling of the pellets in flight can occur in natural fashion, in an environment with controlled temperature (for example, using cooling coils), or in forced fashion using a cold gaseous fluid, such as liquid nitrogen.

Thus, preferably, the temperatures of a cooling area 61 and of the collection area 4 (which may be combined in a single area) are normally monitored and suitably regulated (if necessary).

The characteristics of the method permit production of pellets containing very high percentage weights of active ingredient, normally much higher than 50%. In particular, this can be accomplished by starting from granules 1 containing a percentage weight of active ingredient that is greater than the percentage weight of the encapsulating material. In particular, the granules 1 preferably contain a percentage weight of active ingredient that is greater than or equal to 70%. There is only one constraint on the quantity of active ingredient present in the starting granules 1. This depends on the fact that there must be a quantity of encapsulating material at least sufficient to bind the active principle and to allow, during the step of heating in flight, the formation of a thin surface layer composed essentially of the encapsulating material itself. In particular, for example, the starting granules 1 may be in the form of a porous aggregate of active ingredient in whose pores the encapsulating material is located, the aggregate of active ingredient allowing the encapsulating material, once melted, to percolate relatively easily to the surface of the granule 1.

When the encapsulating material substantially covers the granule 1, the layer thus formed protects the active ingredient contained therein from further degradation, unless the granule 1 (which at this point is already a pellet) is heated further.

This method and the related apparatus, which also forms part of the subject-matter of the present invention and which is described in more detail below, can be used to form composite pellets containing active ingredients of the pharmaceutical type and/or nutritional complements or cosmetics, encapsulated in encapsulating material so as to control the release of the active ingredient in the treatment of humans, or animals, the composite pellets made being of the type containing at least one active ingredient and at least one encapsulating material and typically comprising a substantially uniform surface layer composed primarily of the encapsulating material, and a core in which the active ingredient is present in a greater concentration than in the surface layer.

In a preferred embodiment of the invention, the percentage weight of the active ingredient in the core is higher than the percentage weight of the encapsulating material in the core. In particular, the core contains a percentage weight of active ingredient that is greater than or equal to 70%.

The composition of the finished pellets can be adjusted by adjusting the composition in the starting granules 1, whilst their structure can be adjusted by adjusting the heating time through the efficiency of the heating process and through the length of the first segment 5 of the route from the emission area 3 to the collection area 4.

A particularly important parameter in this respect is constituted by the dimensions of the starting granules 1. Preferably, the granules 1 can have a linear dimension that ranges on average between 100 micrometers and 400 micrometers. In particular, the granules 1 have an average linear dimension of 200 micrometers. Obviously, it is also preferable (but not strictly necessary, depending on circumstances and requirements) for the granules 1 to have a substantially uniform predetermined grain size. In general, the grain size of the starting granules 1 must be regulated on the basis of the surface-to-volume ratio of the set of granules 1 considered in their entirety (for instance referring to a single mass of granules 1) to maximize heating efficiency and reduce the times of exposure to high temperatures to the bare minimum required.

The step of producing the granules 1 can be performed in many different ways that are well-known to experts in the trade, the only restriction being that it must not alter the properties of the active ingredient being used.

In a first variant of the method of the present invention, the step of producing the composite granules 1 comprises at least a step of cold mixing fragments of encapsulating material and fragments of active ingredient in proportions corresponding to the predetermined percentage weights in the granules and a step of cold compressing portions of the mixture thereby obtained to form substantially solid aggregates 11. The aggregates 11 are then ground down to the required grain size to produce the granules 1.

Examples of this granule 1 production process are the processes carried out in cold compacting apparatus such as cold pharmaceutical compressing machines, cold pharmaceutical roto-granulators, where the processes are followed by a grinding step.

In a second variant of the method according to the present invention, where the encapsulating material is soluble in at least one solvent, the production of the composite granules 1 comprises at least the following steps:

treating the encapsulating material with the solvent to reduce it to at least a paste-like state; mixing the encapsulating material with the active ingredient to obtain a mixture at least in a paste-like state; and evaporating the solvent at least once. A subsequent step of grinding portions 12 of the mixture produces granules 1 of the required grain size.

The encapsulating material may be soluble in water, or, if it is a wax or similar material, in acetone. In general any suitable solvent may be used.

A further step of evaporating the solvent may be included after the grinding step or at any other point of the process. Yet another step of recovering the evaporated solvent is preferably also included, especially if the solvent used is potentially toxic.

The solvent evaporating step can be natural, or accomplished by heating the encapsulating material to temperatures below the softening point, or by generating a vacuum in a suitable container in which either the mixture or the portions 12 thereof are positioned (for instance using one or more water pumps or more powerful pumps, such as rotary pumps).

The step of mixing the active ingredient with the encapsulating material may be performed simultaneously with the step of treating the encapsulating material with the solvent.

In yet another variant of the method of the present invention, the production of the composite granules 1 comprises at least the following steps: heating the encapsulating material at least to the temperature at which it softens; mixing the encapsulating material with the active ingredient to obtain a mixture at least in a paste-like state; and grinding portions 12 of the mixture that have at least partially cooled. Cooling is necessary to bring the portions 12 to a consistency such as to enable them to be subjected to grinding without problems.

The steps of heating and mixing may be performed simultaneously.

In both the latter two variants just described, the mixing is preferably performed with mixers, rather than stirrers, since the material is in a paste-like state. Important parameters to be controlled are, for example, the temperature of the mixer and the mechanical mixing energy (for example, the shearing stress of an auger).

To obtain the portions 12 to be ground, an extrusive method can be used (which can also be used for mixing), possibly followed by a step of passing the material through opposing rollers so as to obtain strips and to work the material further.

When necessary, the grinding step can be substituted by a step of granulating the material in a fluid bed, a process that is well known in pharmaceutical technology.

In each of the previous steps of producing the granules 1, the grinding step may be associated with a riddling step designed to separate excessively large granules 1 which can be fed back into the grinder so as to achieve the required degree of grain size uniformity.

In a first variant of the invention, illustrated for example in FIG. 2, the jet 9 of the first gaseous fluid consist of at least two components 9a, 9b concurring with each other on opposite sides of the flow 2 of the granules 1. The jet 9 of the first gaseous fluid may advantageously consist of a plurality of components 9a, 9b concurring with each other all around the flow 2 of the granules 1. For example, there may also be a plurality of jets 9 positioned circumferentially to the direction 21 of the flow 2.

Figure 4:
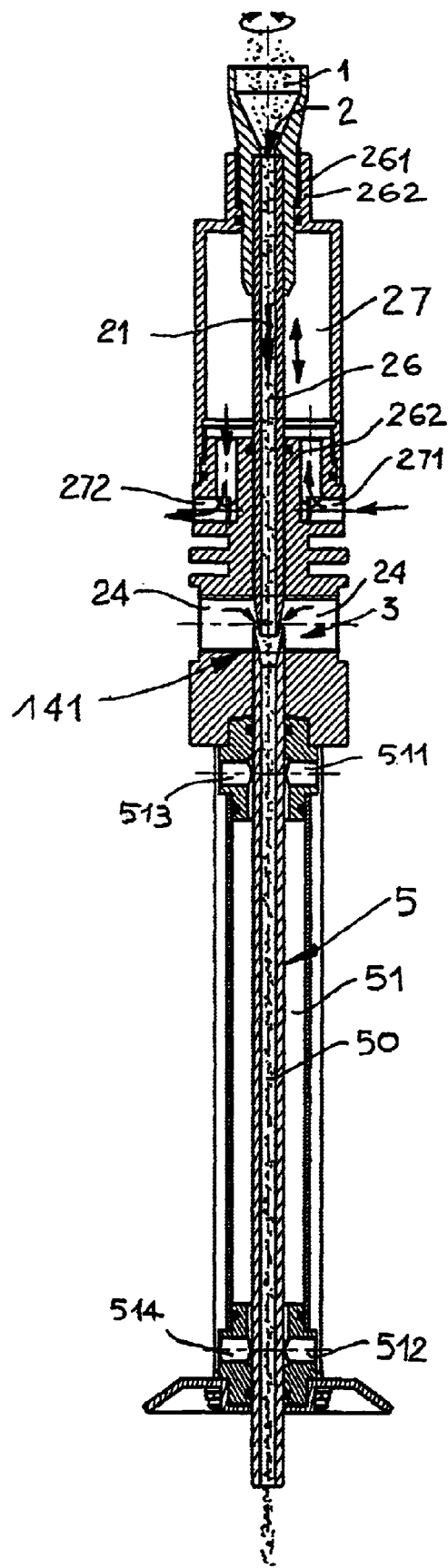
FIG. 4 shows another preferred embodiment of the invention.
Figure 5:
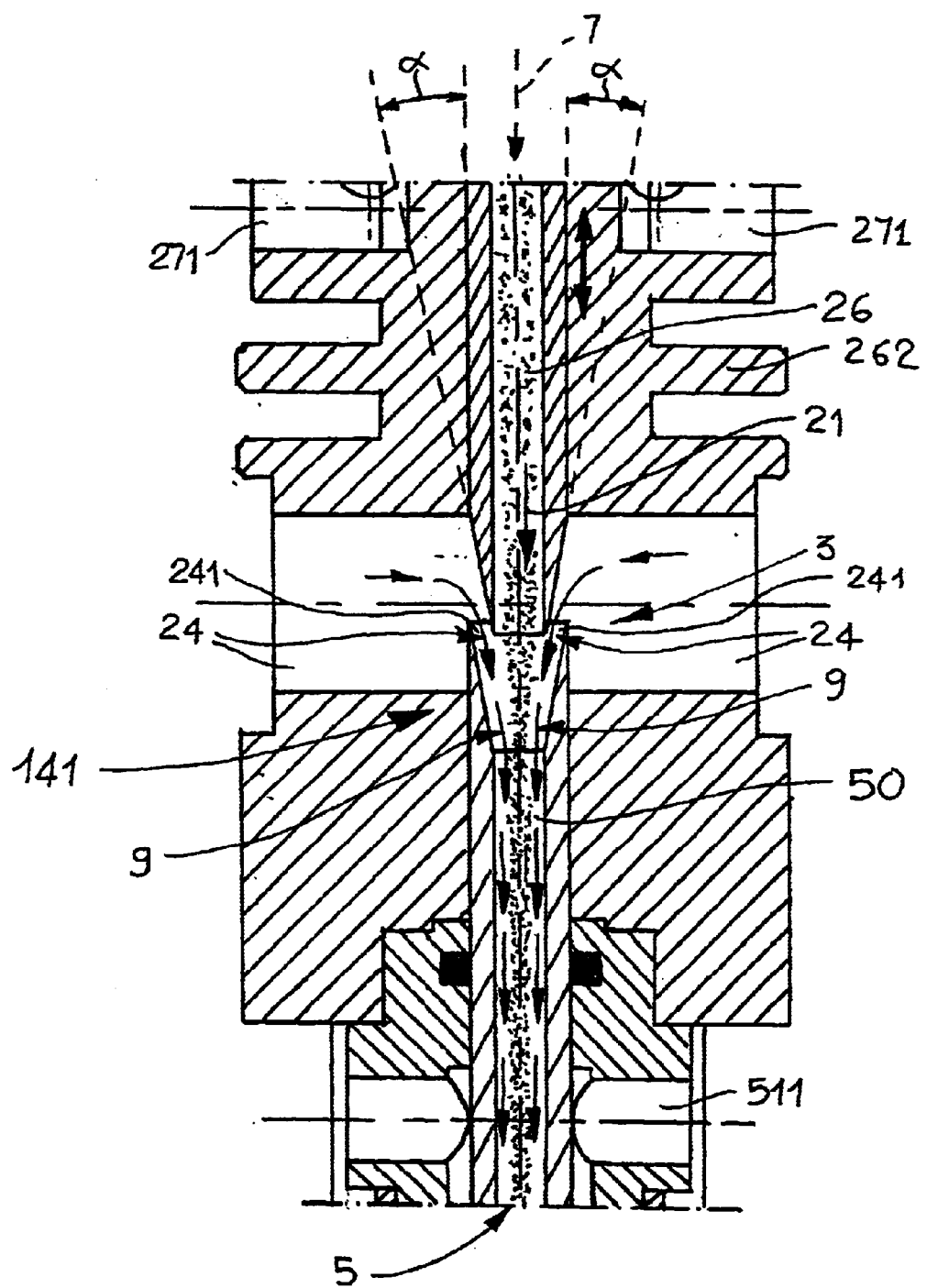
FIG. 5 shows a detail of the embodiment illustrated in FIG. 4.

In a preferred embodiment, shown in FIGS. 4 and 5 (but also in a variant in FIG. 2, where FIG. 2 represents the cross section of section of an object having cylindrical symmetry), the jet 9 of the first gaseous fluid highly advantageously forms a tube of substantially laminar flow which substantially surrounds the flow 2 of the granules 1.

In general, the jet 9 of the first gaseous fluid is guided onto the flow 2 of the granules 1 at a predetermined angle a relative to a direction 21 of the flow 2 of the granules 1. Advantageously, the predetermined angle $\alpha$ is less than 30°. Preferably, the predetermined angle $\alpha$ made with direction 21 of the flow 2 of the granules 1 tends substantially to zero in such a way as to maximize the laminar flow produced.

The flow 2 of the granules 1 can be obtained by a simple gravity feed system.

Preferably, as shown for example in FIGS. 4 and 5, the jet 9 of the first gaseous fluid produces the flow 2 of the granules 1 by suction created by a Venturi effect.

The flow 2 of the granules 1 may also be obtained by driving the granules 1 using a stream 7 of a second gaseous fluid. In this case, by causing the jet 9 of the second gaseous fluid to strike the flow 2 of the granules 1 at a velocity that is greater than the average initial velocity of the granules 1 in the flow 2, heat exchange is improved and, at the same time, a strong Venturi effect may also be produced.

The gaseous fluids used may be filtered, purified or sterile, depending on requirements.

In general, depending on the flow strength of the first gaseous fluid used for heating the granules 1 in flight, it will be necessary to adjust temperature, velocity and transverse dimensions of the heating fluid jet, as well as the number and relative position of the components of the jets 9, according to required productivity and characteristics. In accordance with the values of these parameters, it will be necessary to optimize appropriately the length and/or duration of the route and the geometry of the apparatus.

Advantageously, there may be at least two successive steps of heating the granules 1 in flight along the route. In general, there may be as many in-flight heating steps as are considered necessary for the success of the process. FIG. 3 shows, purely by way of example, a particular procedure for obtaining two or more steps of heating the granules 1 in flight.

Preferably, the method should be implemented at steady thermal state.

The present invention further relates to an apparatus for the implementation of the method described above, schematically illustrated by way of example in FIG. 1.

The apparatus for forming composite pellets containing active ingredients of the pharmaceutical type and/or nutritional complements or cosmetics, encapsulated in encapsulating material so as to control the release of the active ingredient in the treatment of humans or animals comprises, according to the invention, a station 13 for producing substantially solid composite granules 1, containing predetermined percentage weights of at least one encapsulating material and at least one active ingredient, mixed together in substantially homogeneous fashion.

Flow generating means 14 receive the granules 1 from the production station 13 and generate at least one flow 2 of granules 1 along a route from an emission area 3 to a collection area 4 through at least one conduit 26 for the outfeed of the flow 2 of the granules 1 into the emission area 3, which is substantially coaxial with the first segment 5 of the route and forms part of the flow generating means 14.

The apparatus further comprises at least one generator (not illustrated) of at least one jet 9 of a first heated gaseous fluid and at least one conduit 24 for conveying the jet 9 of the first heated gaseous fluid communicating with the emission area 3. The conveying conduit 24 leads the jet 9 to interact with the flow 2 of granules 1 for at least one first segment 5 of the route so as to heat the granules 1 in flight to at least a first temperature. The conveying conduit 24 concurs from at least two opposite sides on the conduit 26 for outfeed into the emission area 3 according to a predetermined angle α to convey the jet 9 of the first heated gaseous fluid onto the flow 2 of the granules 1, in such a way that, starting from the emission area 3, the jet 9 of the first heated gaseous fluid encloses the flow 2 of the granules 1 on at least two opposite sides and in a substantially laminar fashion for at least one first fraction of the first segment 5 of the route the jet 9 of the first heated gaseous fluid and the flow (2) of the granules (1) keeping a substantially common direction of motion along the first fraction of the first segment (5) of the route, said common direction of motion substantially coinciding with the direction of the first fraction of the first segment (5) of the route, the jet (9) of the first heated gaseous fluid tending to trap within it the flow 2 of the granules 1, so as to minimize the risk of prolonged contact of the granules 1 with heated surfaces and to improve the efficiency of heat transfer, the first temperature being high enough to melt at least a portion of encapsulating material located at the surface of each granule 1. This portion of encapsulating material spreads on the surface of each granule 1 to form a substantially uniform surface layer conferring on the granules 1 the form of pellets. The apparatus may comprise means 16 designed to cool the pellets and acting on at least a second segment 6 of the route so as to cool the pellets in flight to at least a second temperature, low enough to cause at least the surface layer to solidify. Means for collecting the pellets collect said pellets at the collection area 4.

Advantageously, the route from the emission area 3 to the collection area 4 is substantially vertical (for instance at least partially within a container 10). In this way it is possible, if necessary, to obtain the flow 2 of granules 1 by letting them fall by gravity using appropriate conveying systems.

Advantageously, the predetermined angle α is less than 30°. Preferably, the predetermined angle α made with direction 21 of the flow 2 of the granules 1 tends substantially to zero in such a way as to maximize the laminar flow. The conveying conduit 24 and the outfeed conduit 26 could, at least for a segment, also be substantially coaxial. In particular the conveying conduit 24 could, at least for a segment of it, be positioned around the outfeed conduit 26. On the angle α, the same considerations made about the method apply.

The jet 9 of the first heated gaseous fluid may be generated by a system similar to a hairdryer, suitably dimensioned, having a blower and a set of electrical resistors. Alternatively, the heating of the first gaseous fluid can take place by passing the first gaseous fluid itself near hot surfaces, or in other equivalent ways (for example by passing the first heated gaseous fluid through a hollow electrical resistor).

On the first gaseous fluid and on the gaseous fluid used for heating the granules 1 in flight, the same considerations made about the same subject in connection with the method can be repeated.

Advantageously, as shown in FIGS. 2 to 4, the conduit 26 for the outfeed of the flow 2 of granules into the emission area 3 comprises a coaxial cooled jacket 27, to protect the granules 1 circulating in the outfeed conduit 26 from overheating. In the cooled jacket 27, for instance, a cooling liquid can be circulated continuously between an inlet 271 and an outlet 272 of the cooled jacket 27 in order to limit the temperature.

Alternatively, or additionally, as shown in FIGS. 2 and 3, means 28 are provided for at least partial thermal insulation between the conduit 26 for the outfeed of the flow 2 of the granules 1 and the jet 9 of the first gaseous fluid, as well as between the outfeed conduit 26 and walls 29 of the emission area in direct contact with the jet 9 of the first gaseous fluid, in order to protect the granules 1 circulating in the outfeed conduit 26 from overheating.

In particular, the thermal insulation means 28 comprise at least one screen 30 coaxial to the outfeed conduit 26 and defining in combination with the outfeed conduit 26 and with the walls 29 of the emission area respectively a first and a second interspace 31, 32. There is also at least one thermal cut-off 33 at least between the outfeed conduit 26 and the screen 30. In this way, at least the first interspace 31 serves as an insulating layer, maintaining a certain temperature differential between the parts of the emission area 3 directly struck by the jet 9 of the first heated gaseous fluid and the outfeed conduit 26, protecting the granules 1 from any overheating (the temperature of the jet 9 just outside the second heating elements 25 might be too high and damage the granules 1).

Advantageously, the coaxial screen 30 extends beyond the outfeed conduit 26 for a predetermined length.

In an embodiment of the invention shown in FIGS. 2 and 3, the first interspace 31 constitutes a thermally insulating layer, whilst the second interspace 32 serves also as an extension of the conveying conduit 24 to favor a tendency to the coaxial condition between the jet 9 of the first gaseous fluid and the flow 2 of the granules 1. In this case, the second interspace 32 is substantially a conduit that is coaxially around the outfeed conduit 26 and constitutes the end portion of the conveying conduit 24.

As shown by way of non-limiting example in FIGS. 4 and 5, the flow generating means 14 comprise the generator (not illustrated) of the jet 9 and means 141 for creating the Venturi effect at the outlet of the outfeed conduit 26. The means 141 for creating the Venturi effect are located at the outlet of the conveying conduit 24 to suck the granules 1 into the emission area 3 and convey them at least along the first segment 5 using the first heated gaseous fluid as the primary fluid.

The flow 2 may thus be generated only in this way, the granules 1 being sucked in automatically. Alternatively, the granules 1 may be driven by a stream 7 of a second gaseous fluid to start generating the flow 2. In this case, however, as stated in connection with the method, the Venturi effect may be used if the velocity of the first gaseous fluid is appropriately greater than the velocity of the second gaseous fluid in the emission area 3. The second gaseous fluid may have all the properties previously described in connection with the method.

In a preferred embodiment, shown by way of example in FIGS. 4 and 5 (but also in a variant in FIGS. 2 and 3, where these represent lengthways sections of an object having cylindrical symmetry), the conveying conduit 24 completely surrounds the outfeed conduit 26 at least for a segment at the point of concurrence on the outfeed conduit 26 itself, in such a way that the jet 9 of the first gaseous fluid forms a tube of substantially laminar flow which substantially completely surrounds the flow 2 of the granules 1.

Advantageously, as shown in FIGS. 4 and 5, in this segment at the point of concurrence on the outfeed conduit 26, the conveying conduit 24 and the outer walls of the outfeed conduit 26 form a gap 241 at the end of the conveyor conduit 24 shaped like a truncated cone, coaxial with the outfeed conduit 26, with predetermined angle α and predetermined thickness, so that the granules 1 are sucked by a Venturi effect through jet 9 of the first heated gaseous fluid. Preferably, the gap 241 leads coaxially into a process conduit 50 whose internal dimension is substantially the same as the internal dimension of the outfeed conduit 26 so as to further favor the formation of the tube of substantially laminar flow.

Conveniently, the inside walls of the process conduit 50 are substantially free of surface roughness so that the jet 9 effectively scrubs the inside walls in order to avoid prolonged contact between the granules 1 and the inside walls themselves. In addition or alternatively, the inside walls of the process conduit 50 can be at least coated with non-stick material so that the jet 9 effectively scrubs the inside walls in order to avoid prolonged contact between the granules 1 and the inside walls themselves. In applications where the temperature need not exceed 200° C., the non-stick material may be teflon.

Advantageously, as shown by the arrows in FIGS. 4 and 5, the thickness of the gap 241 can be adjusted through a guided axial movement of the outfeed conduit 26 relative to the process conduit 50 in order to adjust the velocity of the first heated gaseous fluid in the jet 9 and hence the suction of the granules 1. In particular, as shown in FIG. 4, this movement can be obtained by a lead nut and screw mechanism 261 of the outfeed conduit 26 in its guide 262.

The length of this part of the apparatus (comprising the outfeed conduit 26, the means 141 for creating the Venturi effect and the process conduit 50) may be very short (of the order of one meter in length or even less). The internal diameter of the outfeed conduit 26 and of the process conduit 50 may be very small (a few millimetres). Considering that the outfeed conduit 26 may be directly in contact with the production station 13, the whole apparatus may have a very small size, and provide, at the same time, very high efficiency and productivity.

FIG. 4 also shows that the apparatus comprises a thermal jacket 51 coaxial with the process conduit 50 designed to keep the conduit at the required temperature. In particular, it may be useful to circulate a fluid (for example, water) heated (for example to a temperature from 50° C. to 60° C.) between an inlet and an outlet in order to provide additional heat for the granules 1 which, owing to the very high efficiency of heat exchange with the first heated gaseous fluid in the process conduit 50, would otherwise tend to cool too quickly and to stick to the end (in particular to the outlet) of the process conduit 50, thus obstructing it. The process conduit 50 generally leads into a collection compartment 10 in which a slight negative pressure may be maintained in order to facilitate suction of the granules 1.

The temperatures of both the first gaseous fluid and of the cooling fluid circulating in the coaxial cooled jacket 27 may be measured by suitably located temperature probes to monitor the process and to allow a better feed-back control on it. The temperature of the fluid circulating in the thermal jacket 51 may be monitored and controlled in an analogous way, for instance, by placing two temperature probes, one in a first seat 513 near the inlet 511, and another in a second seat 514 near the outlet 512 of the fluid.

In another embodiment illustrated, for example, in FIGS. 2 and 3, the conduit 24 for conveying the jet 9 of the first gaseous fluid consists of at least two parts 24a, 24b concurring with each other according to a predetermined angle α on opposite sides of the conduit 26 for the outfeed of the flow 2 of the granules 1. Conveniently, the conduit 24 for conveying the jet 9 of the first gaseous fluid consists of a plurality of parts 24a, 24b concurring with each other according to a predetermined angle α all around the conduit 26 for the outfeed of the flow 2 of the granules 1. In this way, it is easier to obtain conditions that approximate the creation by the jet 9 of a tube of laminar flow around the flow 2 of granules 1.

In yet another embodiment, illustrated in the drawings, downstream at least of the outfeed conduit 26 and of the conveying conduit 24, the emission area 3 might comprise lateral walls 38 shaped in such a way as to minimize the effects of turbulence, facilitate steady laminar flow conditions and minimize the risk of prolonged contact of the granules 1 with heated surfaces. Prolonged contact with the heated surfaces, as stated in the course of the discussion of the method, can lead to the damaging or charring of the granules 1 or of the pellets into which they have been transformed, and to risks of fire or precipitation of the active ingredient in the case of biphasic systems.

In a variant of the invention, illustrated in FIG. 3, a global flow 34, constituted by the flow 2 of the heated granules and by the jet 9 of the first heated gaseous fluid, is channeled at least into a second heating stage 35 which comprises at least one additional conduit 36 for conveying an additional jet 37 of a third heated gaseous fluid concurrent with the global flow 34 in order to further heat the granules 1.

The third gaseous fluid may be the same as the first and come from the same generator through a branching of the original conveying conduit 24.

As FIG. 3 clearly shows, the global flow 34 can be channeled into a tubular element similar to the outfeed conduit 26 and all the thermal insulation and temperature control systems described above can be replicated around it.

The additional conveying conduit 36 can concur on the global flow 34 at a certain angle α in a manner similar to the one already described.

Conveniently, the station 13 for producing substantially solid composite granules 1 comprises at least mixing means 39 for at least mixing fragments of active ingredient at least with fragments of encapsulating material to obtain a homogeneous mixture and forming means 40 for forming at least portions 12 of the homogeneous mixture and obtaining at least aggregates 11, 12. The station 13 for producing granules 1 is further provided with granulator means 41 to granulate the aggregates 11, 12.

Advantageously, in general the granulator means 41 can be provided at least with a riddle 47 and, possibly, with a loop 48 for reintroducing into the granulator means 41 granules 1 that are too large to pass the grain size check.

At the outfeed of the forming means 40, the granulator means 41 can comprise at least a fluid bed granulator.

In a preferred embodiment of the invention, shown in FIG. 1, the granulator means 41 alternatively comprise at least a grinder.

In a first embodiment, schematically illustrated in FIG. 1, the mixing means 39 comprise at least one inlet 42 for at least one solvent of the encapsulating material to obtain the homogeneous mixture in the paste state. The inlet 42 may be, as in FIG. 1, the inlet 42 used for the entry of the active ingredient and/or of the encapsulating material, or a separate inlet. Since the mixture to be obtained is in the paste state, the mixing means 39 are preferably mixers. Advantageously, in a preferred embodiment of the invention, the mixing means 39 comprise at least an auger integrated at least partially in an extruder comprised in the forming means 40, to obtain a first fragmentation of the mixture into aggregates 11 and/or into portions 12 of mixture to be worked subsequently.

Advantageously, moreover, in this first embodiment, the station 13 for producing the granules 1 comprises, at least downstream of the forming means 40, at least one substation 43 for the evaporation of the solvent. The evaporation can be natural, or accomplished by heating the encapsulating material to a temperature below the softening point, or by generating a vacuum in a suitable container not explicitly shown in the figure. If grinding is included, obviously the evaporation shall bring the aggregates 11 and/or the portions 12 to the substantially solid state or, in any case, in a state suitable for them to be easily ground down to the required grain size.

Conveniently, moreover, as shown in FIG. 1, to improve the working of the mixture before the possible granulation by the granulator means 41, downstream of the forming means 40 the production station 13 may comprise opposing rollers 46 to bring the aggregates 11, 12 substantially to the shape of thin strips.

Other evaporation stations may be provided, for instance downstream of the station, if any, for grinding the aggregates 11, 12 or simply the portions 12. Preferably, at each solvent evaporation stage, means for recovering the solvent are provided.

As an alternative to mixing with the aid of solvent or to complement such mixing, the mixing means 39 comprise heating elements 44 to heat at least the encapsulating material at least to the softening temperature and to obtain the homogeneous mixture in the paste state. In the presence of an extrusive process similar to the one described above (possibly complemented by working processes with opposing rollers 46), advantageously the heating elements 44 are progressive towards the mouth of the extruder, i.e. the temperature progressively increases towards the mouth of the extruder, as shown by the heating diagram in FIG. 1.

Conveniently, especially in the case in which the granulator means 41 comprise the grinder, the production station 13 comprises, downstream of the forming means 40, at least a cooling sub-station for cooling the aggregates 11, and/or the portions 12. In this way it is easy to bring the aggregates 11 and/or the portions 12 to the substantially solid state or, in any case, in a state suitable for them to be easily ground down to the required grain size.

In a second embodiment, not shown in the figures, if the mixing is dry and it produces a mixture of free fragments of active ingredient and encapsulating material, the forming means 40 may comprise at least a cold compactor, such as a pharmaceutical cold compressing machine or a cold roto-granulator.

Conveniently, the apparatus comprises at least a container 10 that encloses at least the route in a sealed manner to control the atmosphere. All the gaseous fluids used may be filtered, purified or sterilized depending on requirements.

The container 10 may comprise a first flight area 100 without forced cooling and a second area 101 with forced cooling. The second area 101 may be equipped with means for controlling temperature, such as cooling coils, or jets of cold gas (such as those that can be obtained by spraying liquid nitrogen) to cool the pellets in flight The collecting means may be constructed in any way known to an expert in the trade (for example, the bottom of the container 10 may be equipped with a gate valve which can be opened on command and which operates on a riddle and on a collecting system; alternatively, a suction system may be provided, which puts the container 10 in slight depression, thus also aiding the Venturi effect which generates the flow 2 of the granules 1).

The present invention further relates to a composite pellet containing active ingredients of the pharmaceutical type and/or nutritional complements or cosmetics, encapsulated in encapsulating material so as to control the release of the active ingredient in the treatment of humans or animals, the composite pellet made being of the type containing at least one active ingredient and at least one encapsulating material and typically comprising a substantially uniform surface layer composed primarily of the encapsulating material, and a core in which the active ingredient is present in a greater concentration than in the surface layer.

Conveniently, the percentage weight of the active ingredient in the core is higher than the percentage weight of the encapsulating material in the core. Advantageously, the core contains a percentage weight of active ingredient that is greater than 50%. In a preferred embodiment of the invention, the core contains a percentage weight of active ingredient that is greater than or equal to 70%. The encapsulating material can be any suitable material, even one with a high softening and/or melting point.

The encapsulating material can also be a material at least with a low melting point.

The encapsulating material can, furthermore, be a material soluble in at least one solvent. In particular, the encapsulating material can be a material that is at least water-soluble.

The encapsulating materials used can be any of the following, listed purely as non-limiting examples: low melting point, lipophilic materials that are solid at ambient temperature, such as beeswax, carnauba wax, other types of wax, stearic acid, monoglycerides, diglycerides, triglycerides and other substances which are not digestible in the stomach, but can be chemically attacked only by biliary and pancreatic fluids in the intestine; digestible, non gastro-resistant substances; water-soluble substances such as polymers (for example, polyethylene glycols and polyvinylpyrrolidone) which may also have low melting points, and sugars, preferably also with low melting point (for example, xylitol). In cosmetic treatments, any polymers can be used provided they are hypoallergenic and not harmful to health.

In general, any of a very wide variety of active ingredients can be used and, in particular, the active ingredients may be heat-sensitive, as, for example, bioactive ingredients such as yeasts, cells, enzymes, proteins.

The invention achieves important advantages.

First of all, it can increase production efficiency and minimize heat treatment times, making it possible to use encapsulating materials whose melting points are not low and active ingredients that are heat sensitive.

In the second place, it easily provides pellets in which the percentage weight of the active ingredient is preponderant.

A no less important advantage is that of obtaining high productivity with good standards of uniformity in the batches of pellets produced.

Moreover, it permits the use of small sized production facilities, thus reducing costs while at the same time increasing production quality to levels compatible with the treatment of human beings.

The invention described can be subject to modifications and variations without thereby departing from the scope of the inventive concept.

Moreover, all the details of the invention may be substituted by technically equivalent elements.

In practice the materials and dimensions used can be any, depending on requirements.

What is claimed is:

1. An apparatus for forming composite pellets containing active ingredients of the pharmaceutical type and/or nutritional complements or cosmetics, encapsulated in encapsulating material for the controlled release of the active ingredient in the treatment of humans or animals, the apparatus comprising:

a station for producing substantially solid granules;

flow generating means that receive the granules from the production station and generate at least one flow of the granules along a route from an emission area to a collection area;

at least one generator of at least one jet of a first heated gaseous fluid and at least one conduit for conveying the jet of the first heated gaseous fluid communicating with the emission area and leading the jet to interact with the flow of granules for at least one first segment of the route so as to heat the granules in flight to at least a first temperature and confer on the granules the form of pellets;

means for collecting the pellets at the collection area; and wherein the station is designed to produce substantially solid composite granules, containing predetermined percentage weights of at least one encapsulating material and at least one active ingredient, mixed together in substantially homogeneous fashion;

the flow generating means comprise at least one conduit used for the outfeed of the flow of granules into the emission area and being substantially coaxial with the first segment of the route;

the conveying conduit concurring from at least two opposite sides on the conduit for outfeed into the emission area according to a predetermined angle to convey the jet of the first heated gaseous fluid onto the flow of the granules, in such a way that, starting from the emission area, the jet of the first heated gaseous fluid encloses the flow of the granules on at least two opposite sides and in a substantially laminar fashion for at least one first fraction of the first segment of the route, the jet of the first heated gaseous fluid and the flow of the granules keeping a substantially common direction of motion along the first fraction of the first segment of the route, said common direction of motion substantially coinciding with the direction of the first fraction of the first segment of the route, the jet of the first heated gaseous fluid tending to trap within it the flow of the granules, so as to minimize the risk of prolonged contact of the granules with heated surfaces of the apparatus and to improve the efficiency of heat transfer, the first temperature being high enough to melt at least a portion of encapsulating material located at the surface of each granule, this portion of encapsulating material spreading on the surface of each granule to form a substantially uniform surface layer so as to confer on the granules the form of pellets.

2. The apparatus according to claim 1, wherein the flow generating means comprise the generator of the jet and means for creating the Venturi effect at the outlet of the outfeed conduit, the means for creating the Venturi effect being located at the outlet of the conveying conduit to suck the granules into the emission area and convey them at least along the first segment using the first heated gaseous fluid as the primary fluid.

3. The apparatus as in claim 1, wherein the angle made with the direction of the flow of the granules tends substantially to zero.

4. The apparatus as in claim 2, wherein the angle made with the direction of the flow of the granules tends substantially to zero.

5. The apparatus according to claim 1, wherein the conveying conduit completely surrounds the outfeed conduit at least for a segment at the point of concurrence on the outfeed conduit itself, in such a way that the jet of the first gaseous fluid forms a tube of substantially laminar flow which substantially completely surrounds the flow of the granules.

6. The apparatus according to claim 2, wherein the conveying conduit completely surrounds the outfeed conduit at least for a segment at the point of concurrence on the outfeed conduit itself, in such a way that the jet of the first gaseous fluid forms a tube of substantially laminar flow which substantially completely surrounds the flow of the granules.

7. The apparatus as in claim 5, wherein in the segment at the point of concurrence on the outfeed conduit, the conveying conduit and the outer walls of the outfeed conduit form a gap at the end of the conveyor conduit shaped like a truncated cone, coaxial with the outfeed conduit, with predetermined angle and predetermined thickness, so that the granules are sucked by the Venturi effect through jet of the first heated gaseous fluid.

8. The apparatus as in claim 6, wherein in the segment at the point of concurrence on the outfeed conduit, the conveying conduit and the outer walls of the outfeed conduit form a gap at the end of the conveyor conduit shaped like a truncated cone, coaxial with the outfeed conduit, with predetermined angle and predetermined thickness, so that the granules are sucked by the Venturi effect through jet of the first heated gaseous fluid.

9. The apparatus as in claim 7, wherein the gap leads coaxially into a process conduit whose internal dimension is substantially the same as the internal dimension of the outfeed conduit so as to further favor the formation of the tube of substantially laminar flow.

10. The apparatus as in claim 8, wherein the gap leads coaxially into a process conduit whose internal dimension is substantially the same as the internal dimension of the outfeed conduit so as to further favor the formation of the tube of substantially laminar flow.

11. The apparatus as in claim 9 or 10, wherein the inside walls of the process conduit are substantially free of surface roughness so that the jet effectively scrubs the inside walls in order to avoid prolonged contact between the granules and the inside walls themselves.

12. The apparatus as in claim 9 or 10, wherein the inside walls of the process conduit are at least coated with non-stick material so that the jet effectively scrubs the inside walls in order to avoid prolonged contact between the granules and the inside walls themselves.

13. The apparatus as in claim 9 or 10, wherein the thickness of the gap can be adjusted through a guided axial movement of the outfeed conduit relative to the process conduit in order to adjust the velocity of the first heated gaseous fluid in the jet and hence the suction of the granules.

14. The apparatus as in claim 9, comprising a thermal jacket coaxial with the process conduit designed to keep the conduit at the required temperature.

15. The apparatus as in claim 10, comprising a thermal jacket coaxial with the process conduit designed to keep the conduit at the required temperature.

16. The apparatus as in claim 1, wherein the conduit for conveying the first gaseous fluid consists of at least two parts that are concurrent with each other on opposite sides of the conduit for the outfeed of the granules according to the predetermined angle.

17. The apparatus as in claim 2, wherein the conduit for conveying the first gaseous fluid consists of at least two parts that are concurrent with each other on opposite sides of the conduit for the outfeed of the granules according to the predetermined angle.

18. The apparatus as in claim 1, wherein the conduit for conveying the first gaseous fluid consists of a plurality of parts that are concurrent with each other all around the conduit for the outfeed of the granules according to the predetermined angle.

19. The apparatus as in claim 2, wherein the conduit for conveying the first gaseous fluid consists of a plurality of parts that are concurrent with each other all around the conduit for the outfeed of the granules according to the predetermined angle.

20. The apparatus as in claim 1, wherein the conduit for the outfeed of the flow of granules into the emission area comprises a coaxial cooled jacket designed to protect the granules circulating in the outfeed conduit from overheating.

21. The apparatus as in claim 2, wherein the conduit for the outfeed of the flow of granules into the emission area comprises a coaxial cooled jacket designed to protect the granules circulating in the outfeed conduit from overheating.

22. The apparatus as in claim 5, wherein the conduit for the outfeed of the flow of granules into the emission area comprises a coaxial cooled jacket designed to protect the granules circulating in the outfeed conduit from overheating.

23. The apparatus as in claim 6, wherein the conduit for the outfeed of the flow of granules into the emission area comprises a coaxial cooled jacket designed to protect the granules circulating in the outfeed conduit from overheating.

24. The apparatus as in claim 7, wherein the conduit for the outfeed of the flow of granules into the emission area comprises a coaxial cooled jacket designed to protect the granules circulating in the outfeed conduit from overheating.

25. The apparatus as in claim 8, wherein the conduit for the outfeed of the flow of granules into the emission area comprises a coaxial cooled jacket designed to protect the granules circulating in the outfeed conduit from overheating.

26. The apparatus as in claim 9, wherein the conduit for the outfeed of the flow of granules into the emission area comprises a coaxial cooled jacket designed to protect the granules circulating in the outfeed conduit from overheating.

27. The apparatus as in claim 10, wherein the conduit for the outfeed of the flow of granules into the emission area comprises a coaxial cooled jacket designed to protect the granules circulating in the outfeed conduit from overheating.

28. The apparatus as in claim 14, wherein the conduit for the outfeed of the flow of granules into the emission area comprises a coaxial cooled jacket designed to protect the granules circulating in the outfeed conduit from overheating.

29. The apparatus as in claim 15, wherein the conduit for the outfeed of the flow of granules into the emission area comprises a coaxial cooled jacket designed to protect the granules circulating in the outfeed conduit from overheating.

30. The apparatus as in claim 16, wherein the conduit for the outfeed of the flow of granules into the emission area comprises a coaxial cooled jacket designed to protect the granules circulating in the outfeed conduit from overheating.

31. The apparatus as in claim 17, wherein the conduit for the outfeed of the flow of granules into the emission area comprises a coaxial cooled jacket designed to protect the granules circulating in the outfeed conduit from overheating.

32. The apparatus as in claim 18, wherein the conduit for the outfeed of the flow of granules into the emission area comprises a coaxial cooled jacket designed to protect the granules circulating in the outfeed conduit from overheating.

33. The apparatus as in claim 19, wherein the conduit for the outfeed of the flow of granules into the emission area comprises a coaxial cooled jacket designed to protect the granules circulating in the outfeed conduit from overheating.

34. The apparatus as in claim 20, comprising means for at least partial thermal insulation between the conduit for the outfeed of the flow of the granules and the jet of the first gaseous fluid, as well as between the outfeed conduit and walls of the emission area in direct contact with the jet of the first gaseous fluid, in order to protect the granules circulating in the outfeed conduit from overheating.

35. The apparatus as in claim 21, comprising means for at least partial thermal insulation between the conduit for the outfeed of the flow of the granules and the jet of the first gaseous fluid, as well as between the outfeed conduit and walls of the emission area in direct contact with the jet of the first gaseous fluid, in order to protect the granules circulating in the outfeed conduit from overheating.

36. The apparatus as in claim 22, comprising means for at least partial thermal insulation between the conduit for the outfeed of the flow of the granules and the jet of the first gaseous fluid, as well as between the outfeed conduit and walls of the emission area in direct contact with the jet of the first gaseous fluid, in order to protect the granules circulating in the outfeed conduit from overheating.

37. The apparatus as in claim 23, comprising means for at least partial thermal insulation between the conduit for the outfeed of the flow of the granules and the jet of the first gaseous fluid, as well as between the outfeed conduit and walls of the emission area in direct contact with the jet of the first gaseous fluid, in order to protect the granules circulating in the outfeed conduit from overheating.

38. The apparatus as in claim 30, comprising means for at least partial thermal insulation between the conduit for the outfeed of the flow of the granules and the jet of the first gaseous fluid, as well as between the outfeed conduit and walls of the emission area in direct contact with the jet of the first gaseous fluid, in order to protect the granules circulating in the outfeed conduit from overheating.

39. The apparatus as in claim 31, comprising means for at least partial thermal insulation between the conduit for the outfeed of the flow of the granules and the jet of the first gaseous fluid, as well as between the outfeed conduit and walls of the emission area in direct contact with the jet of the first gaseous fluid, in order to protect the granules circulating in the outfeed conduit from overheating.

40. The apparatus as in claim 32, comprising means for at least partial thermal insulation between the conduit for the outfeed of the flow of the granules and the jet of the first gaseous fluid, as well as between the outfeed conduit and walls of the emission area in direct contact with the jet of the first gaseous fluid, in order to protect the granules circulating in the outfeed conduit from overheating.

41. The apparatus as in claim 33, comprising means for at least partial thermal insulation between the conduit for the outfeed of the flow of the granules and the jet of the first gaseous fluid, as well as between the outfeed conduit and walls of the emission area in direct contact with the jet of the first gaseous fluid, in order to protect the granules circulating in the outfeed conduit from overheating.

42. The apparatus as in claim 34, wherein the thermal insulation means comprise:
- at least one screen coaxial to the outfeed conduit and defining in combination with the outfeed conduit and with the walls of the emission area respectively a first and a second interspace;
- at least one thermal cut-off at least between the outfeed conduit and the screen.

43. The apparatus as in claim 35, wherein the thermal insulation means comprise:
- at least one screen coaxial to the outfeed conduit and defining in combination with the outfeed conduit and with the walls of the emission area respectively a first and a second interspace;
- at least one thermal cut-off at least between the outfeed conduit and the screen.

44. The apparatus as in claim 36, wherein the thermal insulation means comprise:
- at least one screen coaxial to the outfeed conduit and defining in combination with the outfeed conduit and with the walls of the emission area respectively a first and a second interspace;
- at least one thermal cut-off at least between the outfeed conduit and the screen.

45. The apparatus as in claim 37, wherein the thermal insulation means comprise:
- at least one screen coaxial to the outfeed conduit and defining in combination with the outfeed conduit and with the walls of the emission area respectively a first and a second interspace;
- at least one thermal cut-off at least between the outfeed conduit and the screen.

46. The apparatus as in claim 38, wherein the thermal insulation means comprise:
- at least one screen coaxial to the outfeed conduit and defining in combination with the outfeed conduit and with the walls of the emission area respectively a first and a second interspace;
- at least one thermal cut-off at least between the outfeed conduit and the screen.

47. The apparatus as in claim 39, wherein the thermal insulation means comprise:
- at least one screen coaxial to the outfeed conduit and defining in combination with the outfeed conduit and with the walls of the emission area respectively a first and a second interspace;
- at least one thermal cut-off at least between the outfeed conduit and the screen.

48. The apparatus as in claim 40, wherein the thermal insulation means comprise:
- at least one screen coaxial to the outfeed conduit and defining in combination with the outfeed conduit and with the walls of the emission area respectively a first and a second interspace;
- at least one thermal cut-off at least between the outfeed conduit and the screen.

49. The apparatus as in claim 41, wherein the thermal insulation means comprise:
- at least one screen coaxial to the outfeed conduit and defining in combination with the outfeed conduit and with the walls of the emission area respectively a first and a second interspace;
- at least one thermal cut-off at least between the outfeed conduit and the screen.

50. The apparatus as in claim 42, wherein the coaxial screen extends beyond the outfeed conduit for a predetermined length.

51. The apparatus as in claim 43, wherein the coaxial screen extends beyond the outfeed conduit for a predetermined length.

52. The apparatus as in claim 44, wherein the coaxial screen extends beyond the outfeed conduit for a predetermined length.

53. The apparatus as in claim 45, wherein the coaxial screen extends beyond the outfeed conduit for a predetermined length.

54. The apparatus as in claim 46, wherein the coaxial screen extends beyond the outfeed conduit for a predetermined length.

55. The apparatus as in claim 47, wherein the coaxial screen extends beyond the outfeed conduit for a predetermined length.

56. The apparatus as in claim 48, wherein the coaxial screen extends beyond the outfeed conduit for a predetermined length.

57. The apparatus as in claim 49, wherein the coaxial screen extends beyond the outfeed conduit for a predetermined length.

58. The apparatus as in claim 42, wherein the first interspace constitutes a thermally insulating layer, whilst the second interspace serves also as an extension of the conveying conduit to favor a tendency to the coaxial condition between the jet of the first gaseous fluid and the flow of the granules.

59. The apparatus as in claim 42, wherein the first interspace constitutes a thermally insulating layer, whilst the second interspace serves also as an extension of the conveying conduit to favor a tendency to the coaxial condition between the jet of the first gaseous fluid and the flow of the granules.

60. The apparatus as in claim 44, wherein the first interspace constitutes a thermally insulating layer, whilst the second interspace serves also as an extension of the conveying conduit to favor a tendency to the coaxial condition between the jet of the first gaseous fluid and the flow of the granules.

61. The apparatus as in claim 45, wherein the first interspace constitutes a thermally insulating layer, whilst the second interspace serves also as an extension of the conveying conduit to favor a tendency to the coaxial condition between the jet of the first gaseous fluid and the flow of the granules.

62. The apparatus as in claim 46, wherein the first interspace constitutes a thermally insulating layer, whilst the second interspace serves also as an extension of the conveying conduit to favor a tendency to the coaxial condition between the jet of the first gaseous fluid and the flow of the granules.

63. The apparatus as in claim 47, wherein the first interspace constitutes a thermally insulating layer, whilst the second interspace serves also as an extension of the conveying conduit to favor a tendency to the coaxial condition between the jet of the first gaseous fluid and the flow of the granules.

64. The apparatus as in claim 48, wherein the first interspace constitutes a thermally insulating layer, whilst the second interspace serves also as an extension of the conveying conduit to favor a tendency to the coaxial condition between the jet of the first gaseous fluid and the flow of the granules.

65. The apparatus as in claim 49, wherein the first interspace constitutes a thermally insulating layer, whilst the second interspace serves also as an extension of the conveying conduit to favor a tendency to the coaxial condition between the jet of the first gaseous fluid and the flow of the granules.

66. The apparatus as in claim 1, wherein a global flow, constituted by the flow of the heated granules and by the jet of the first heated gaseous fluid, is channeled at least into a second heating stage which comprises at least one additional conduit for conveying an additional jet of a third heated gaseous fluid concurrent with the global flow in order to further heat the granules.

67. The apparatus as in claim 1, wherein, downstream at least of the outfeed conduit and of the conveying conduit, the emission area comprises lateral walls shaped to minimize the effects of turbulence, facilitate steady laminar flow conditions and minimize the risk of prolonged contact of the granules with heated surfaces.

68. The apparatus as in claim 1, comprising means for cooling the pellets acting on at least a second segment of the route to cool the pellets in flight to at least a second temperature, low enough to cause at least the surface layer to solidify.

69. The apparatus as in claim 1, wherein the station for producing the substantially solid composite granules comprises at least the following:

mixing means for mixing at least fragments of active ingredient with at least fragments of encapsulating material to obtain a homogeneous mixture;

means for forming at least portions of the homogeneous mixture and obtaining at least aggregates;

granulator means to granulate the aggregates.

70. The apparatus as in claim 69, wherein the mixing means comprise third heating elements for heating at least the encapsulating material at least to the softening temperature to obtain the homogeneous mixture in the paste state.

71. The apparatus as in claim 70, wherein the production station comprises, downstream of the forming means, at least one cooling sub-station for cooling the aggregates.

72. The apparatus of claim 69, 70 or 71, wherein the granulator means comprise at least one fluid-bed granulator.

* * * * *